(12) United States Patent
Yu (10) Patent No.: US 11,565,037 B2
(45) Date of Patent: Jan. 31, 2023

(54) TRANSFUSION GUIDING ROBOT AND GUIDING METHOD

(71) Applicant: BOE TECHNOLOGY GROUP CO., LTD., Beijing (CN)

(72) Inventor: Zhanquan Yu, Beijing (CN)

(73) Assignee: BOE TECHNOLOGY GROUP CO., LTD., Beijing (CN)

(*) Notice: Subject to any disclaimer, the term of this patent is extended or adjusted under 35 U.S.C. 154(b) by 1199 days.

(21) Appl. No.: 16/078,244

(22) PCT Filed: Dec. 15, 2017

(86) PCT No.: PCT/CN2017/116540
§ 371 (c)(1),
(2) Date: Aug. 21, 2018

(87) PCT Pub. No.: WO2018/188367
PCT Pub. Date: Oct. 18, 2018

(65) Prior Publication Data
US 2021/0213193 A1 Jul. 15, 2021

(30) Foreign Application Priority Data

Apr. 14, 2017 (CN) .......................... 201710244255.6

(51) Int. Cl.
*A61M 5/14* (2006.01)
*B25J 11/00* (2006.01)
(Continued)

(52) U.S. Cl.
CPC .......... *A61M 5/1415* (2013.01); *B25J 11/008* (2013.01); *G05D 1/0055* (2013.01);
(Continued)

(58) Field of Classification Search
CPC ........ A61M 5/1415; A61M 2205/3375; A61M 2205/35; A61M 2209/082;
(Continued)

(56) References Cited

U.S. PATENT DOCUMENTS

| 2005/0269464 A1* | 12/2005 | Adelman | A61M 5/1414 248/170 |
| 2011/0238029 A1* | 9/2011 | Biset | A61J 1/10 604/410 |
| 2012/0197464 A1* | 8/2012 | Wang | G06T 15/10 701/28 |

(Continued)

FOREIGN PATENT DOCUMENTS

| CN | 104898652 A | 9/2015 |
| CN | 205041882 U | 2/2016 |

(Continued)

OTHER PUBLICATIONS

Translation of CN-106421963-A (Year: 2017).*
First Office Action dated Mar. 18, 2019 corresponding to Chinese application No. 201710244255.6.
(Continued)

*Primary Examiner* — Kenneth J Malkowski
*Assistant Examiner* — Ibrahim Abdoalatif Alsomairy
(74) *Attorney, Agent, or Firm* — Nath, Goldberg & Meyer; Joshua B. Goldberg (57) ABSTRACT

Embodiments of the disclosure provide a transfusion guiding robot and a guiding method for guiding a movement of a transfused person. The transfusion guiding robot comprises a controller, a moving portion and a fixing portion. The controller is configured to receive and process instruction information, and control the transfusion guiding robot according to the instruction information; the moving portion is configured to move according to a command from the
(Continued)

controller; and the fixing portion is configured to fix a container, a height of the fixing portion being adjustable.

18 Claims, 4 Drawing Sheets

(51) Int. Cl.
*G05D 1/02* (2020.01)
*G05D 1/00* (2006.01)

(52) U.S. Cl.
CPC ......... *G05D 1/0212* (2013.01); *G05D 1/0231* (2013.01); *G05D 1/0242* (2013.01); *G05D 1/0255* (2013.01); *A61M 2205/3375* (2013.01); *A61M 2205/35* (2013.01); *A61M 2209/082* (2013.01)

(58) Field of Classification Search
CPC ............ A61M 2205/505; B25J 11/008; G05D 1/0055; G05D 1/0212; G05D 1/0231; G05D 1/0242; G05D 1/0255; G05D 1/00; G05D 1/02; G05D 1/0214; G05D 1/024; G05D 1/0257; G05D 1/0285
See application file for complete search history.

(56) References Cited

U.S. PATENT DOCUMENTS

| | | |
|---|---|---|
| 2015/0366546 A1 | 12/2015 | Kamen et al. |
| 2017/0140890 A1* | 5/2017 | Tsang ................... G08B 21/187 |
| 2020/0009417 A1* | 1/2020 | Dalebout ........... A63B 21/4043 |

FOREIGN PATENT DOCUMENTS

| | | | | |
|---|---|---|---|---|
| CN | 106075636 A | | 11/2016 | |
| CN | 106421963 A | * | 2/2017 | .......... A61M 5/1415 |
| CN | 106421963 A | | 2/2017 | |
| JP | 200424305 A | | 1/2004 | |

OTHER PUBLICATIONS

International Search Report dated Mar. 21, 2018 corresponding to application No. PCT/CN2017/116540.

* cited by examiner

TRANSFUSION GUIDING ROBOT AND GUIDING METHOD

This is a National Phase Application filed under 35 U.S.C. 371 as a national stage of PCT/CN2017/116540, filed Dec. 15, 2017, an application claiming the benefit of Chinese Patent Application No. 201710244255.6 filed on Apr. 14, 2017, the contents of which are hereby incorporated by reference in its entirety as part of this application.

FIELD

Embodiments of the present disclosure relate to a transfusion guiding robot and a guiding method.

BACKGROUND

In modern medicine, transfusion is an important part of drug treatment. Taking antibiotic treatment as an example, in the United Kingdom, approximate 40% of patients treated with antibiotics are administrated via transfusion. Although doctors will try to dispense oral medications once the patient's condition improves, the transfusions are often the first choice for treatment.

SUMMARY

An embodiment of the disclosure provides a transfusion guiding robot for guiding a movement of a transfused person, comprising a controller, a moving portion and a fixing portion, wherein the controller is configured to receive and process instruction information, and control the transfusion guiding robot according to the instruction information; the moving portion is configured to move according to a command from the controller; and the fixing portion is configured to fix a container, a height of the fixing portion being adjustable.

Optionally, the transfusion guiding robot further comprises a main body, configured to hold the controller, the moving portion, and the fixing portion.

Optionally, the main body comprises a base, a support post and a bracket, the support post is fixedly connected to the base, the bracket is located above the support post and is movable up and down with respect to the support post, and the fixing portion is provided on the bracket.

Optionally, a periphery of a top portion of the support post is provided with a ring-shaped handle, which provides a support for the transfused person.

Optionally, the moving portion comprises a moving member and a driving circuit, wherein the moving member is disposed underneath the base of the main body unit and configured to drive the transfusion guiding robot to move; and the driving circuit is disposed inside the base of the main body unit, coupled to the moving member and configured to supply power to the mobile member.

Optionally, the moving member comprises at least three omni-directional moving wheels which are uniformly disposed underneath the base of the main body; and at least one of the omni-directional moving wheels is coupled to the driving circuit and receives the power supplied from the driving circuit.

Optionally, the moving portion further comprises an obstacle avoidance module device, which is disposed on a periphery of the base of the main body unit, and which is configured to send detected obstacle information to the controller such that the controller updates the command according to the obstacle information; and the moving portion is moved according to an updated command.

As an alternative, the transfusion guiding robot further comprises a navigation device, configured to construct an environment map, establish a movement route in the environment map, and send the movement route to the controller.

Optionally, the moving portion further comprises an obstacle avoidance device, which is disposed on a periphery of the base of the main body, and which is configured to send detected obstacle information to the navigation device in real time; and the navigation device updates the movement route according to the obstacle information and sends an updated movement route to the controller.

Optionally, the navigation device comprises a laser radar, which is disposed on a periphery of the base of the main body, and which is configured to detect a distance and an orientation of an object in the environment from the transfusion guiding robot and send distance and orientation information to the navigation device.

Optionally, the obstacle avoidance device comprises at least one of infrared sensors and ultrasonic sensors which are uniformly disposed on the periphery of the base of the main body.

Optionally, the controller comprises an interaction device, and the controller is configured to receive a command input from the transfused person through the interaction device and send the command input from the transfused person to the moving portion.

Optionally, the interaction device comprises a voice interaction device or a mobile terminal device.

Optionally, the fixing portion comprises a fixing base defining an internal space and a pair of clamping pieces, and the pair of clamping pieces are disposed in the internal space of the fixing base and configured to clamp the container.

Optionally, the pair of clamping pieces are movably disposed in the internal space of the fixing base, and the fixing portion further comprises tension springs and slide rails, wherein the slide rails are disposed on opposite two inner sides of the fixing base and configured to restrict the pair of clamping pieces from moving along the slide rails; and the tension springs are disposed on the other two inner sides of the fixing base where the slide rails are not located and configured to urge the pair of clamping pieces toward each other.

Optionally, the tension springs are disposed in pair on the other two inner sides of the fixing base where the slide rails are not located.

Optionally, the fixing portion further comprises a friction plate, which is disposed on an internal wall of the clamping piece and which has a laminated structure with elasticity and uneven surface.

Optionally, the fixing base is formed as a rectangular frame, and an outer wall of each clamping piece matches the internal space of the fixing base and an internal wall of each clamping piece is in a semi-circular shape.

Optionally, the transfusion guiding robot further comprises a safety device, configured to detect a distance between the transfused person and the transfusion guiding robot in real time to adjust a power output of the driving circuit.

Optionally, the safety device comprises a cord coupled to the main body; a sensor provided on a periphery of the cord; and a hand ring formed in a closed loop at an end of the cord.

Optionally, the cord is formed of a resilient material, and the sensor is configured to detect a tension received by the cord and send a magnitude of the tension to the controller.

In another aspect, an embodiment of the disclosure also provides a guiding method for guiding a movement of a transfused person, applicable to the transfusion guiding robot as set forth above, and comprising steps of: receiving and processing instruction information; and controlling the transfusion guiding robot according to the instruction information, wherein the step of controlling the transfusion guiding robot according to the instruction information comprises detecting an obstacle to generate obstacle information; updating an instruction according to the obstacle information; and moving the transfusion guiding robot according to an updated instruction.

BRIEF DESCRIPTION OF THE DRAWINGS

FIG. 2a is a schematic diagram illustrating a main body and a moving portion in FIG. 1a;

FIGS. 3 and 4 are schematic diagrams of a fixing portion in FIG. 1a;

DETAILED DESCRIPTION OF THE EMBODIMENTS

In order that those skilled in the art can better understand the technical solutions of the present disclosure, the transfusion guiding robot of the present disclosure will be further described in detail below in conjunction with the accompanying drawings and specific implementations.

During the transfusion, due to limitation of liquid supply position, a transfused person usually sits or lies in a certain place, and it is difficult for the transfused person to move due to a connection between his or her body part and an infusion container. When the transfused person would like to move (for example, there is a need for toilet), his or her family member or a nurse usually holds the infusion container, and assists the transfused person to slowly move to the destination. In the case that a bathroom is difficultly found in a completely unfamiliar hospital environment, it will inevitably cause a great inconvenience to transfused persons and their family members. In addition, at the end of the transfusion, if there is no call ringing around a transfused person, the transfused person or his/her family member needs to go to a nurse station to call a nurse to change liquid or pull out a needle. This is also not easy for a sick transfused person or his/her family member.

It can be seen that there is a need to design a device that can automatically guide the transfused person to independently reach a preset destination and can cause the transfused person to maintain a smooth communication with the nurse at any time.

The present disclosure provides a transfusion guiding robot in view of the deficiencies in the related art. The transfusion guiding robot at least partially solves the inconvenience of the transfused person. At the same time, the transfusion guiding robot can also cause transfused person to maintain a smooth communication with the nurse.

In one aspect, an embodiment of the disclosure provides a conveniently controlled transfusion guiding robot. The transfusion guiding robot can assist the transfused person to move, thereby solving the problem that the transfused person is difficult to move in the transfusion process. The transfused person here refers in general to a patient who is being transfused, an accompanying family member of the transfused patient, or a user of auxiliary equipment that can perform similar transfusions.

The embodiment of the present disclosure has the following advantageous effects. The transfusion guiding robot can conveniently and automatically guide the transfused person. In addition, if necessary, the transfused person can maintain a smooth communication with the nurse through the transfusion guiding robot. Therefore, the transfusion guiding robot of the present disclosure effectively solves the problem that the transfused person is difficult to move in the transfusion process.

Figure 1A:
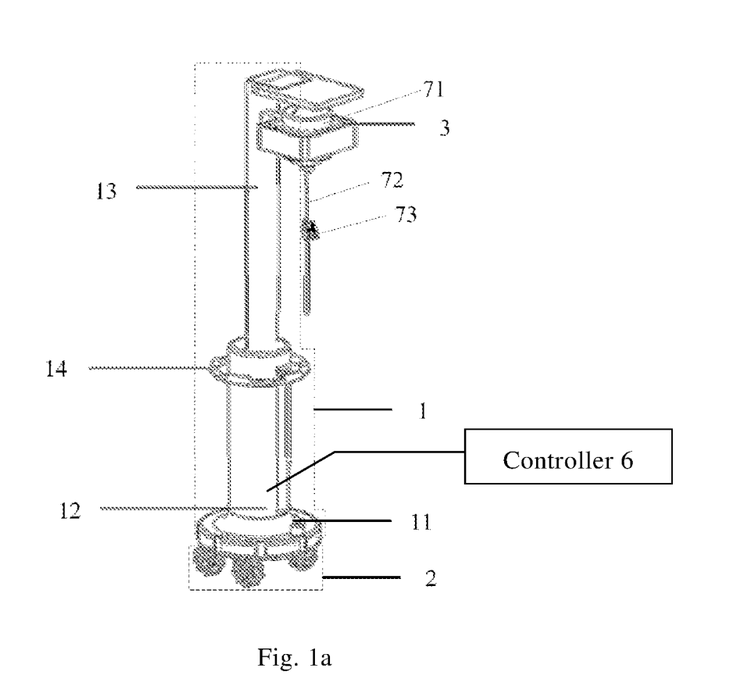
FIG. 1a is a schematic diagram of an overall structure of a transfusion guiding robot according to an embodiment of the present disclosure.

According to this embodiment, there is provided a transfusion guiding robot for guiding a movement of a transfused person. As shown in FIG. 1a, the transfusion guiding robot may include a controller 6, a moving portion 2, a fixing portion 3, and a main body 1, wherein the controller 6 is configured to receive and process instruction information, and control the transfusion guiding robot according to the instruction information;

the moving portion 2 is configured to move according to a command from the controller 6; and the fixing portion 3 is configured to fix a container 71, a height of the fixing portion being adjustable; and the main body 1 is configured to hold the controller 6, the moving portion 2, and the fixing portion 3.

Figure 1B:
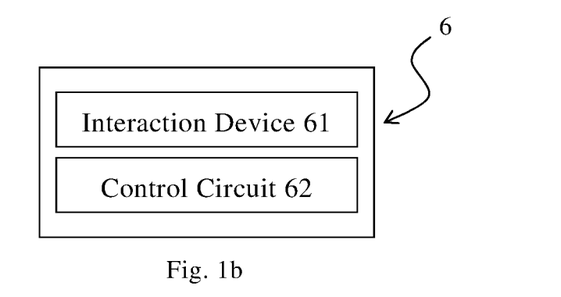
FIG. 1b is a block diagram illustrating a structure of a controller.

The controller 6 provides the transfused person with a human-machine interaction interface. For example, the controller 6 may include a microprocessor (MPU), and an input device such as a voice interaction device 61 and/or a touch screen. The instruction information includes but is not limited to an instruction to start and close the transfusion guiding robot, an instruction to drive the moving portion 2, an instruction to drive the fixing portion 3 to ascend and descend, an instruction to call the nurse, for example. The instruction information may also include any suitable instructions that can be input through the voice interaction device 61 and/or the touch screen and/or a mobile terminal device and processed by the microprocessor. The fixing portion 3 can fix the container filled with liquid. For the sake of clarity, the structural schematic diagram of FIG. 1a illustrates the container 71 fixed by the fixing portion 3 in the operating state, and also illustrates a transfusion tube 72 underneath the container 71 and a liquid regulation valve 73 arranged on the transfusion tube 72. The moving portion 2 includes omni-directional moving wheels 22 so as to realize the controllable transfusion guiding robot.

Figure 2A:
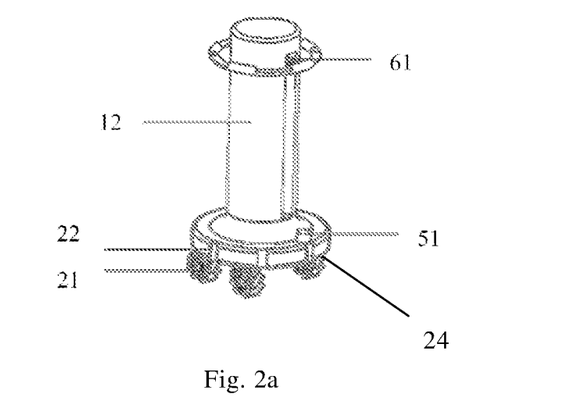

As shown in FIG. 2a, the main body 1 includes a base 11, a support post 12, and a bracket 13. The support post 12 is fixedly connected to the base 11. The bracket 13 is located above the support post 12 and can move up and down with respect to the support post 12. The fixing portion 3 is provided on the bracket 13. Since the fixing portion 3 is provided on the bracket 13 and the bracket 13 can be moved up and down with respect to the support post 12, a height of the container 71 fixed by the fixing portion 3 can be adjusted according to a height of the transfused person. Here, the base 11 may be integrally formed or detachably connected with the support post 12. The connection between the base 11 and the support post 12 is not limited herein.

A periphery of a top portion of the support post 12 is provided with a ring-shaped handle 14, which can provide a support for the transfused person. The handle 14 can be used as a simple walking aid to facilitate the movement of the transfused person in the case where the transfused person may have mobility inconvenience.

Figure 2B:
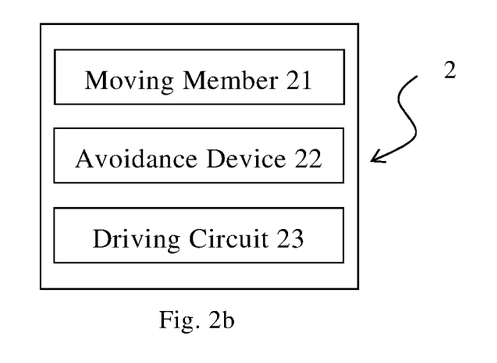
FIG. 2b is a block diagram illustrating a structure of the moving portion.

The moving portion 2 includes a moving member 21 and a driving circuit 23. The moving member 21 is disposed underneath the base 11 of the main body 1 and is configured to drive the transfusion guiding robot to move. The driving circuit 23 is disposed inside the base 11 of the main body 1, coupled to the moving member 21 and configured to supply power to the mobile member 21.

Optionally, as shown in FIG. 2b, the moving member 21 includes at least three omni-directional moving wheels which are uniformly disposed underneath the base 11 of the main body 1. At least one of the omni-directional moving wheels 21 is coupled to the driving circuit and can receive the power supplied from the driving circuit.

In view of possible obstacles in the environment, the moving portion 2 may further include an obstacle avoidance device 22. The obstacle avoidance device 22 is disposed on a periphery of the base 11 of the main body 1, and is configured to send detected obstacle information to the controller 6 in real time so that the controller 6 updates the command including destination information according to the obstacle information; and the moving portion 2 is moved according to the updated command.

Optionally, the obstacle avoidance device 22 includes a plurality of infrared sensors and/or ultrasonic sensors 24, which are uniformly disposed on the periphery of the base 11 of the main body 1. Of course, the obstacle avoidance device 22 may also include any members having an emission-reflection ranging function. Therefore, the obstacle avoidance device 22 herein is not limited to include an infrared sensor or an ultrasonic sensor.

In the transfusion guiding robot according to this embodiment, the controller 6 includes an interaction device 61 and a control circuit 62. The controller 6 is configured to receive a command input from a transfused person through the interaction device 61 and send the command input from the transfused person to the moving portion 2. The controller 6 is a central control member for controlling and routing the moving portion 2 in the transfusion guiding robot and is a key to automatic control. Currently, the controller 6 can be achieved through a smart control chip burning program.

In the controller 6, for example, the interaction device 61 may include an input device such as a voice interaction device and/or a touch screen. As an alternative, a mobile terminal device (including a computer, a PAD, or a mobile phone, for example) can also be used as an interactive device. The transfused person can input a destination through the mobile terminal device or through his or her voice. Further, the transfused person can control the movement of the robot by voice. In addition, the transfused person can also call a nurse or talk with a nurse or doctor by the robot.

It is easy to understand that the stability of the container 7 (e.g., a transfusion bag or transfusion bottle) is critical, as a device for providing the transfused patient with equipment aid movement. The transfusion bag or transfusion bottle is fixed to the main body 1 by the fixing portion 3, and can ascend and descend with respect to the main body 1 through the bracket 13. In the transfusion guiding robot according to this embodiment, the fixing portion 3 includes a fixing base 31 defining an internal space and a pair of clamping pieces 33. The pair of clamping pieces 33 are disposed in the internal space of the fixing base 31 and configured to clamp the container 7. Since the fixing portion 3 securely fixes the transfusion bag or the transfusion bottle, it is no longer necessary for the patient, the accompanying person or the nurse to raise the transfusion bag or the transfusion bottle.

Figure 3:
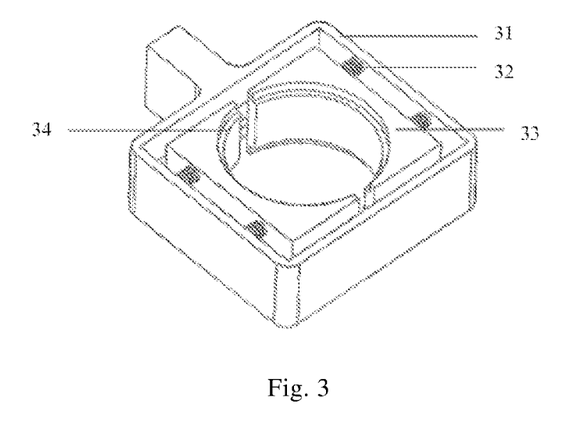
Figure 4:
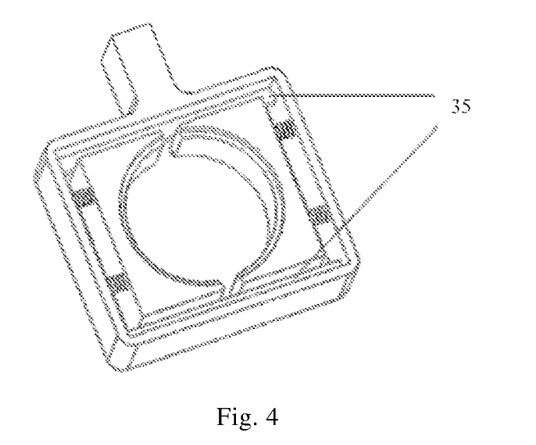

As shown in FIGS. 3 and 4, the pair of clamping pieces 33 are movably disposed in the internal space of the fixing base 31, and the fixing portion 3 further includes tension springs 32 and slide rails 35, wherein the slide rails 35 are disposed on opposite sides of the fixing base 31 and configured to restrict the pair of clamping pieces 33 from moving along the slide rails; and the tension springs 32 are disposed on opposite sides of the fixing base 31 where the slide rails 35 are not located and configured to urge the pair of clamping pieces 33 toward each other. By means of the fixing portion 3, it is possible to fix transfusion bags or transfusion bottles with various sizes.

Further optionally, the tension springs 32 are disposed in pair on opposite sides of the fixing base 31 where the slide rails are not located. By the arrangement of the tension springs 32 and the slide rails 35, the pair of clamping pieces trend to move toward the internal space of the fixing base 31, thereby ensuring that it is possible to clamp and fix the transfusion bag or the transfusion bottle with different shapes.

Further optionally, the fixing portion 3 further includes a friction plate 34. The friction plate 34 is disposed on an internal wall of the clamping piece 33 and has a laminated structure with elasticity and uneven surface. For example, the friction plate 34 is formed from a rubber material. The friction plates 34 can increase a frictional force to further ensure the stability of clamping the container.

Here, the fixing base 31 is formed as a rectangular frame, an outer wall of each clamping piece 33 matches the internal space of the fixing base 31 and an internal wall of each clamping piece 33 is in a semi-circular shape. By the shape matching of the fixing base 31 and the clamping piece 33, the stability of clamping the container can be further ensured.

In this embodiment, the transfused person can control the transfusion guiding robot by means of voice input or manual input. During the equipment aid movement, the transfusion guiding robot can avoid obstacles by the detection of the obstacle avoidance sensor until reaching destination.

Compared to the above-described embodiments, the transfusion guiding robot according to this embodiment further includes a navigation device such that the transfusion guiding robot can automatically guide a person being transfused to a fixed position.

Figure 1C:
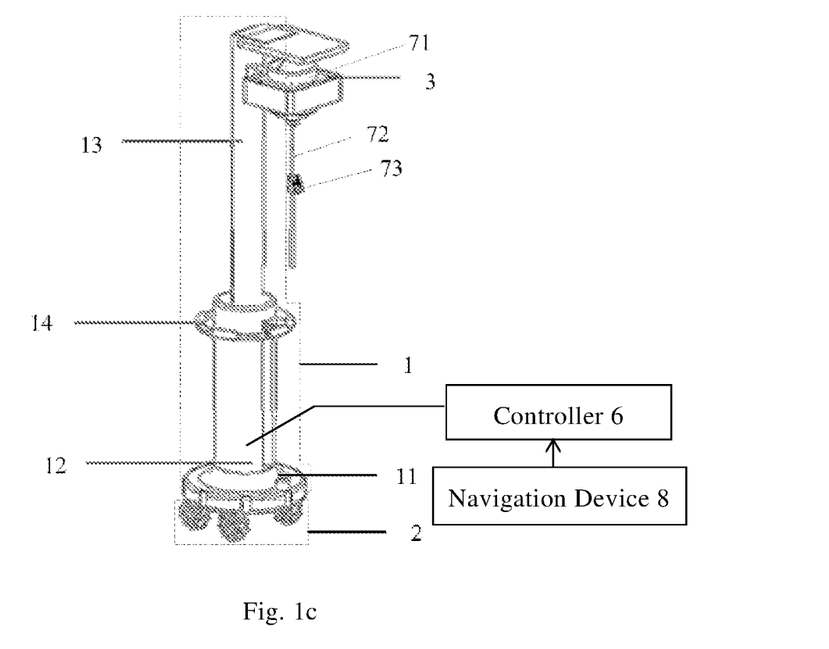
FIG. 1c is a schematic diagram of an overall structure of a transfusion guiding robot according to an embodiment of the present disclosure.

To facilitate the guidance of the transfused person to a destination (for example, toilet), the transfusion guiding robot may further include a navigation device 8, which is configured to construct an environment map, establish a movement route in the environment map, and send the movement route to the controller 6.

Similar to the above embodiment, in view of the possible obstacles in the environment, in this embodiment, the moving portion 2 may further include an obstacle avoidance device 22. The obstacle avoidance device 22 is disposed on a periphery of the base 11 of the main body 1, and is configured to send detected obstacle information to the navigation device 8 in real time. The navigation device 8 updates the movement route according to the obstacle information and sends the updated movement route to the controller 6.

Referring to FIG. 2a, the navigation device includes a laser radar 51. The laser radar 51 is disposed on a periphery of the base 11 of the main body 1, and is configured to detect a distance and an orientation of an object in the environment from the transfusion guiding robot and send distance and orientation information to the navigation device 8. Automatic navigation can be achieved by the navigation device to automatically guide the transfused person.

In the transfusion guiding robot according to this embodiment, the controller 6 includes an interaction device 61 and a control circuit 62. The controller 6 is configured to receive a command inputted from a transfused person through the interaction device 61, and send the command input from the transfused person to the navigation device 8. The navigation device 8 can generate a movement route based on a current position of the transfused person and a target position. The moving portion 2 can move according to the movement route.

The transfusion guiding robot according to this embodiment can efficiently help the transfused person safely travel through the laser radar 51 and the obstacle avoidance sensor.

In this embodiment, the transfusion guiding robot may plan the movement route through the navigation device 8. During the equipment aid movement, the obstacle avoidance sensor 22 detects an obstacle in the surrounding environment and sends the obstacle information to the navigation device 8. The navigation device 8 can update the movement route in real time based on the obstacle information to avoid obstacles.

Figure 5:
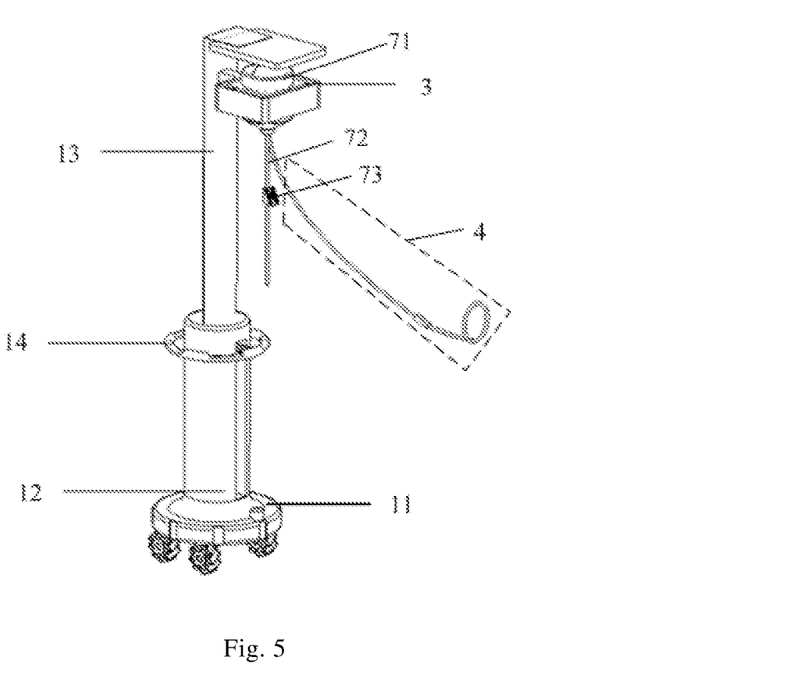
FIG. 5 is a schematic diagram of an overall structure of a transfusion guiding robot according to an embodiment of the present disclosure.

Compared with the above embodiment, as shown in FIG. 5, the transfusion guiding robot according to this embodiment further includes a safety device 4. The safety device 4 is configured to detect a distance between the transfused person and the transfusion guiding robot in real time to adjust a power output of the driving circuit 23. The safety device 4 can ensure that the distance between the transfused person and the transfusion guiding robot falls within an appropriate range.

Figure 6:
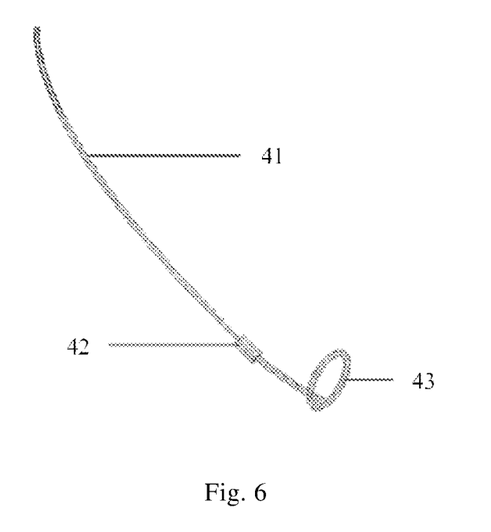
FIG. 6 is a schematic diagram of a safety device in FIG. 5.

Reference can be made to FIG. 6 for more detail. The safety device 4 includes a cord 41 coupled to the main body 1; a sensor 42 provided on a periphery of the cord 41; and a hand ring 43 formed in a closed loop at an end of the cord 41. According to this embodiment, the hand ring 43 may be worn on the transfused person's wrist, thereby ensuring that the distance between the transfused person and the transfusion guiding robot is within an appropriate range. The cord 41 is formed of a resilient material. The sensor 42 may be a tension sensor configured to detect a tension received by the cord and send a magnitude of the tension to the controller 6. In a normal case, the transfused person follows the transfusion guiding robot and is coupled to the transfusion guiding robot via the resilient cord 41. When the tension sensor is subject to the tension, the transfusion guiding robot will slow down. Of course, the cord and the sensor can also be selected from other components or structures as long as they can judge whether the distance between the transfused person and the transfusion guiding robot exceeds a predetermined range.

Of course, the transfused person can also interact with the robot by voice. For example, the transfused person can control a speed of the robot by voice.

With the transfusion guiding robots according to the first to third embodiments, the transfused person can be automatically and easily guided. In addition, if necessary, the transfused person can maintain a smooth communication with the nurse through the transfusion guiding robot. Therefore, the transfusion guiding robot according to the present disclosure effectively solves the problem that the transfused person has a difficulty in movement during the transfusion.

In another aspect, the present disclosure also includes a guiding method for guiding a movement of a transfused person. The guiding method is applicable to the transfusion guiding robot according to the embodiments of the present disclosure, and includes steps of:

receiving and processing instruction information; and controlling the transfusion guiding robot according to the instruction information.

The step of controlling the transfusion guiding robot according to the instruction information may include: detecting an obstacle to generate obstacle information; updating an instruction according to the obstacle information; and moving the transfusion guiding robot according to an updated instruction.

Before moving the transfusion guiding robot according to the updated instruction, the step of controlling the transfusion guiding robot according to the instruction information may further include: constructing an environment map and establishing a movement route in the environment map; and updating the movement route according to the obstacle information.

It can be understood that the above embodiments are merely exemplary embodiments provided for illustrating the principle of the present disclosure. However, the present disclosure is not limited thereto. For a person of ordinary skill in the art, various variations and improvements may be made without departing from the spirit and essence of the present disclosure, and these variations and improvements are also considered to be within the scope of the present disclosure.

What is claimed is:

1. A transfusion guiding robot for guiding a movement of a transfused person, comprising a controller, a moving portion and a fixing portion, wherein the controller is configured to receive and process instruction information, and control the transfusion guiding robot according to the instruction information;

the moving portion is configured to move according to a command from the controller; and the fixing portion is configured to fix a container, a height of the fixing portion being adjustable, wherein the fixing portion comprises a fixing base defining an internal space and a pair of clamping pieces, the pair of clamping pieces being movably disposed in the internal space of the fixing base and configured to clamp the container, and wherein the fixing portion further comprises tension springs and slide rails, the slide rails being disposed on opposite two inner sides of the fixing base and configured to restrict the pair of clamping pieces from moving along the slide rails, and the tension springs being disposed on the other two inner sides of the fixing base where the slide rails are not located and configured to urge the pair of clamping pieces toward each other.

2. The transfusion guiding robot according to claim 1, further comprising a main body, configured to hold the controller, the moving portion, and the fixing portion, wherein the main body comprises a base, a support post and a bracket, the support post is fixedly connected to the base, the bracket is located above the support post and is movable up and down with respect to the support post, and the fixing portion is provided on the bracket.

3. The transfusion guiding robot according to claim 2, wherein a periphery of a top portion of the support post is provided with a ring-shaped handle, which provides a support for the transfused person.

4. The transfusion guiding robot according to claim 2, wherein the moving portion comprises a moving member and a driving circuit, wherein the moving member is disposed underneath the base of the main body and configured to drive the transfusion guiding robot to move; and the driving circuit is disposed inside the base of the main body, coupled to the moving member and configured to supply power to the moving member.

5. The transfusion guiding robot according to claim 4, wherein the moving member comprises at least three omni-directional moving wheels which are uniformly disposed underneath the base of the main body; and at least one of the omni-directional moving wheels is coupled to the driving circuit and receives the power supplied from the driving circuit.

6. The transfusion guiding robot according to claim 4, wherein the moving portion further comprises an obstacle avoidance device, which is disposed on a periphery of the base of the main body, and which is configured to send detected obstacle information to the controller in real time such that the controller updates the command according to the obstacle information; and the moving portion moves according to an updated command.

7. The transfusion guiding robot according to claim 4, further comprising a navigation device, configured to construct an environment map, establish a movement route in the environment map, and send the movement route to the controller.

8. The transfusion guiding robot according to claim 7, wherein the moving portion further comprises an obstacle avoidance device, which is disposed on a periphery of the base of the main body, and which is configured to send detected obstacle information to the navigation device in real time; and the navigation device updates the movement route according to the obstacle information and sends an updated movement route to the controller.

9. The transfusion guiding robot according to claim 7, wherein the navigation device comprises a laser radar, which is disposed on a periphery of the base of the main body, and which is configured to detect a distance and an orientation of an object in the environment from the transfusion guiding robot and send distance and orientation information to the navigation device.

10. The transfusion guiding robot according to claim 6, wherein the obstacle avoidance device comprises at least one of infrared sensors and ultrasonic sensors uniformly disposed on the periphery of the base of the main body.

11. The transfusion guiding robot according to claim 1, wherein the controller comprises an interaction device, and the controller is configured to receive a command input from the transfused person through the interaction device and send the command input from the transfused person to the moving portion.

12. The transfusion guiding robot according to claim 1, wherein the tension springs are disposed in pair on the other two inner sides of the fixing base where the slide rails are not located.

13. The transfusion guiding robot according to claim 1, wherein the fixing portion further comprises a friction plate, which is disposed on an internal wall of the clamping piece and which has a laminated structure with elasticity and uneven surface.

14. The transfusion guiding robot according to claim 1, wherein the fixing base is a rectangular frame, and an outer wall of each clamping piece matches the internal space of the fixing base and an internal wall of each clamping piece is in a semi-circular shape.

15. The transfusion guiding robot according to claim 4, further comprising a safety device, configured to detect a distance between the transfused person and the transfusion guiding robot in real time to adjust a power output of the driving circuit.

16. The transfusion guiding robot according to claim 15, wherein the safety device comprises a cord coupled to the main body; a sensor provided on a periphery of the cord; and a hand ring formed in a closed loop at an end of the cord.

17. The transfusion guiding robot according to claim 16, wherein the sensor is configured to detect a tension received by the cord and send a magnitude of the tension to the controller.

18. A guiding method for guiding a movement of a transfused person, comprising steps of:

adjusting a height of a fixing portion of a transfusion guiding robot and fixing a container by the fixing portion, wherein the fixing portion comprises a fixing base defining an internal space and a pair of clamping pieces, the pair of clamping pieces being movably disposed in the internal space of the fixing base and configured to clamp the container, and wherein the fixing portion further comprises tension springs and slide rails, the slide rails being disposed on opposite two inner sides of the fixing base and configured to restrict the pair of clamping pieces from moving along the slide rails, and the tension springs being disposed on the other two inner sides of the fixing base where the slide rails are not located and configure to urge the pair of clamping pieces toward each other;

receiving and processing instruction information; and controlling the transfusion guiding robot according to the instruction information, wherein the controlling the transfusion guiding robot according to the instruction information comprises: detecting an obstacle to generate obstacle information; updating an instruction according to the obstacle information; and moving the transfusion guiding robot according to an updated instruction.

\* \* \* \* \*